United States Patent
Annegarn et al.

(10) Patent No.: US 10,524,698 B2
(45) Date of Patent: Jan. 7, 2020

(54) FALL DETECTION SYSTEM AND METHOD

(71) Applicant: KONINKLIJKE PHILIPS N.V., Eindhoven (NL)

(72) Inventors: Janneke Annegarn, Eindhoven (NL); Heribert Baldus, Aachen (DE); Warner Rudolf Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 422 days.

(21) Appl. No.: 14/895,369

(22) PCT Filed: May 23, 2014

(86) PCT No.: PCT/EP2014/060607
§ 371 (c)(1),
(2) Date: Dec. 2, 2015

(87) PCT Pub. No.: WO2014/195146
PCT Pub. Date: Dec. 11, 2014

(65) Prior Publication Data
US 2016/0113551 A1 Apr. 28, 2016

(30) Foreign Application Priority Data
Jun. 6, 2013 (EP) .................................... 13170775

(51) Int. Cl.
*A61B 5/11* (2006.01)
*A61B 5/00* (2006.01)
(Continued)

(52) U.S. Cl.
CPC ............ *A61B 5/1117* (2013.01); *A61B 5/486* (2013.01); *A61B 5/7275* (2013.01);
(Continued)

(58) Field of Classification Search
CPC ..... A61B 5/1117; A61B 5/486; A61B 5/7275; A61B 5/7282; A61B 5/7475; G08B 21/043; G08B 21/0446; G08B 31/00
(Continued)

(56) References Cited

U.S. PATENT DOCUMENTS 5,976,083 A * 11/1999 Richardson .......... A61B 5/0245 482/8
2007/0061600 A1 * 3/2007 Kuroda ................. G06F 1/3203 713/300
(Continued)

FOREIGN PATENT DOCUMENTS

JP 2012501780 A 1/2012
JP 2012505683 A 3/2012
(Continued)

OTHER PUBLICATIONS

Narayanan et al: "Evaluation of Falls Risk Using a Single, Waist-Mounted Tri-Axial Accelerometer"; Thesis, The University of New South Wales, 2011, 236 Page Document.
(Continued)

*Primary Examiner* — Daniel L Cerioni

(57) ABSTRACT

There is provided a fall detection system, comprising a user device comprising one or more sensors for measuring the movements of a user; and the system further comprising a processing unit configured to operate in a first mode in which the processing unit processes the measured movements to determine if the user has fallen and a further mode in which the processing unit processes measured movements obtained during a user-specified time period to determine the risk of the user falling.

16 Claims, 6 Drawing Sheets

(51) Int. Cl.
*G08B 21/04* (2006.01)
*G08B 31/00* (2006.01)
*G16H 50/30* (2018.01)
*A61B 17/00* (2006.01)

(52) U.S. Cl.
CPC ............ *A61B 5/7282* (2013.01); *A61B 5/742* (2013.01); *A61B 5/7475* (2013.01); *G08B 21/043* (2013.01); *G08B 21/0446* (2013.01); *G08B 31/00* (2013.01); *G16H 50/30* (2018.01); *A61B 2017/00207* (2013.01); *A61B 2560/0475* (2013.01); *A61B 2562/0219* (2013.01)

(58) Field of Classification Search
USPC .......................................................... 600/595
See application file for complete search history.

(56) References Cited

U.S. PATENT DOCUMENTS

| | | | | |
|---|---|---|---|---|
| 2007/0113725 | A1* | 5/2007 | Oliver | A61B 5/02438 84/612 |
| 2012/0119904 | A1 | 5/2012 | Coleman Boone et al. | |
| 2012/0314901 | A1 | 12/2012 | Hanson et al. | |
| 2014/0276130 | A1* | 9/2014 | Mirelman | A61B 5/744 600/483 |
| 2014/0285435 | A1* | 9/2014 | Bezos | G06F 1/1626 345/156 |

FOREIGN PATENT DOCUMENTS

| | | |
|---|---|---|
| WO | 2004114245 A1 | 12/2004 |
| WO | 2010029478 A1 | 3/2010 |
| WO | 2010044013 A1 | 4/2010 |
| WO | 2010126878 A1 | 11/2010 |
| WO | 2011004322 A1 | 1/2011 |
| WO | 2012146957 A1 | 11/2012 |
| WO | 2013054257 A1 | 4/2013 |

OTHER PUBLICATIONS

Caporusso et al: "A Pervasive Solution for Risk Awareness in the Context of Fall Prevention"; Pervasivehealth, 2009, pp. 1-8.

Paoli et al: "A System for Ubiquitous Fall Monitoring at Home Via a Wireless Sensor Network and a Wearable Mote"; Expert Systems With Applications, 39 (2012), pp. 5566-5575.

Shany et al: "Sensors-Based Wearable Systems for Monitoring of Human Movement and Falls"; IEEE Sensors Journal, vol. 12, No. 3, Mar. 2012, pp. 658-670.

* cited by examiner

FALL DETECTION SYSTEM AND METHOD

CROSS-REFERENCE TO PRIOR APPLICATIONS

This application is the U.S. National Phase application under 35 U.S.C. § 371 of International Application No. PCT/EP2014/060607, filed on May 23, 2014, which claims the benefit of European Patent Application No. 13170775.4, filed on Jun. 6, 2013. These applications are hereby incorporated by reference in their entirety herein.

TECHNICAL FIELD OF THE INVENTION

The invention relates to a fall detection system that is for detecting falls by a user, and in particular relates to a fall detection system that also enables a user to quickly and easily estimate their fall risk in a non-clinical environment.

BACKGROUND TO THE INVENTION

Falls are one of the greatest health risk factors for elderly people. About one third of older people above the age of 65 fall at least once a year.

Many of these falls could be avoided by early identification of fall risk and the application of effective and targeted fall prevention programs. In particular, home-based fall prevention exercise programs that include balance training, muscle strengthening and a walking plan have been shown to be effective in reducing the occurrence of falls.

Thus, fall risk assessments are carried out on users to identify those at high risk of falling, and the exercises selected for the fall prevention program are tailored to the user to maximise their benefit in reducing the fall risk.

In some cases, a fall risk assessment can be made by the user filling in a questionnaire to provide a subjective estimate of their fall risk. For example the user can fill in the "Review your risk" questionnaire at the website www.learn-nottofall.com. The answers to the questionnaire can be used to provide feedback in the form of advice and recommended exercises for minimising the fall risk.

In other cases, caregivers or healthcare professionals can provide a much better estimation of fall risk by making an objective assessment of physical performance, which can be based for example on walking (including an assessment of the user's gait), strength, balance including standing still) and reaction time. One particular assessment involves the 'sit-to-stand' (STS) transfer which can be used as a strength and balance performance measure and thus a measure of fall risk. In this assessment, the power exerted by the user in standing up from a sitting position is measured. Other assessments include a timed-up-and-go (TUG) test in which the user stands up from a chair, walks a certain distance and returns to the chair. The time the user consumes in doing so is a measure of their fall risk. More elaborate assessments include the Physiological Profile Assessment (PPA) in which a set of multiple characteristics are evaluated.

However, for objectively determining fall risk, people are required to regularly present themselves at a clinic, where typically expensive dedicated hardware and clinicians are located. This way of assessing fall risk is costly. The need to make and keep to appointments results in a low monitoring/observation rate by the users. In many cases, people only present themselves for the first time at the clinic after a fall has occurred, and it may be that the earlier application of a fall prevention program could have prevented that fall from occurring.

Thus, it is desirable to be able to obtain an objective measurement of a user's fall risk while they are in their home environment without assistance from or visiting a care provider or healthcare professional. However, individuals do not want to buy bulky and expensive dedicated hardware like a camera system, a treadmill or a force plate that needs to be installed in the home. Moreover, the need for individuals to have to set up complex test environments should be avoided.

It is known in the art to provide devices that collect long-term movement data of normal daily behaviour and that calculate a fall risk from the long-term movement data. For example US 2012/0119904 describes the use of a pedometer that monitors the steps taken by the patient during the day. However, this information is gathered in free living conditions and its usefulness in determining fall risk is limited as it largely depends on the environmental challenges (e.g. stairs) and the movement intention of the individual. Also information on the physical capabilities that enable the individual to adequately respond to unforeseen events (such as a stumble) to prevent a fall cannot be accurately captured. Another problem is that a large amount of data needs to be collected, which means that a large battery is required since the device has to be collecting and storing and/or processing the data for a long period of time.

Thus, there is a need for a system and method that enables a user (and/or a remotely-located clinician) to quickly and easily estimate the user's fall risk in a home or other non-clinical environment while ensuring that the user-worn or carried device remains generally unobtrusive and does not result in the user having to carry or wear additional hardware.

SUMMARY OF THE INVENTION

Many individuals at risk of falling carry or wear a fall detection device that monitors their movements and determines when a fall has occurred. When a fall is detected, the device can trigger an alarm and/or contact a call centre (in some cases via a base unit in the user's home) to request help for the user.

In accordance with the invention, functionality for determining a user's fall risk and fall detection functionality are incorporated into a single fall detection system. This is advantageous since an estimation of fall risk can be determined using measurements obtained using the sensors typically found in fall detection devices, reducing the need for the user to carry additional hardware.

To obtain the measure of fall risk the user has to perform certain movements or exercises while wearing or carrying a user device. The device (or a processing unit in a base unit associated with the user device) analyses the performance of these movements or exercises from the measurements of the movement of the user obtained by the sensor(s) in the user device and thus determines the fall risk.

Although it may be possible to automatically detect these movements and exercises by analysing the movement measurements, it is necessary in this case for the movement measurements to be continuously collected and processed. In addition, even when a movement or exercise is detected, it is not possible to determine the intention of the user, which can be important in determining the actual fall risk. For example, when performing an unsupervised exercise or movement for determining a fall risk, the user may be required to perform that exercise or movement as quickly as possible or for as long as possible, i.e. in order to test the physical capability of the user when performing these exercises. However, those movements or exercises may also occur during the user's normal daily activities, but the user will not be trying to perform them for, e.g. as quickly or as long as they can. In that case, an estimation of fall risk based on analysis of those movements or exercises during normal daily activities may result in an inaccurate estimation in the fall risk for the user.

To solve these problems, the system is configured to receive an indication from the user specifying a time period in which they have or will perform exercises or movements relevant to estimating a fall risk. This avoids the need for the system to continuously analyse the movement measurements to identify when the user has performed a specified movement or exercise, thus reducing power consumption, and also provides an indication of the user's intention to perform the movements or exercises to estimate their fall risk.

Thus, according to a first aspect of the invention, there is provided a fall detection system, comprising a user device comprising one or more sensors for measuring the movements of a user; and the system further comprising a processing unit configured to operate in a first mode in which the processing unit processes the measured movements to determine if the user has fallen and a further mode in which the processing unit processes measured movements obtained during a user-specified time period to determine the risk of the user falling.

In preferred embodiments the processing unit is configured to detect a first input from the user specifying the start of the time period during which the user will perform one or more exercises and/or movements used to assess fall risk.

Preferably, on detection of the first input from the user, the processing unit is configured to operate in a data collection mode in which measured movements are stored in a memory module for use by the processing unit when the processing unit is operating in the further mode.

In some embodiments, on detection of the first input from the user specifying the start of the time period, the processing unit is further configured to start a timer. In that case, the processing unit is preferably configured to resume operating in the first mode when the timer reaches a predetermined value.

In alternative embodiments, the processing unit is configured to resume operating in the first mode on detection of a second input from the user specifying the end of the time period.

In some embodiments, the processing unit is configured to operate in the further mode on detection of a third input from the user.

In some embodiments, the system further comprises a display that is controlled by the processing unit, the processing unit being configured to provide instructions to the user via the display for one or more exercises and/or movements for the user to perform while the processing unit is operating in the data collection mode.

In some embodiments, the processing unit is configured to adapt the instructions for the one or more exercises and/or movements based on a previously-determined fall risk for the user.

Preferably, the processing unit is configured to continue processing the measured movements to determine if the user has fallen while operating in the data collection mode.

Preferably, the processing unit is configured to switch to operating in the first mode in the event that it is determined that the user has fallen while the processing unit is operating in the data collection mode.

In some embodiments the system further comprises any of (i) a button or key connected to the processing device for the user to press to provide the input(s); (ii) a display connected to the processing device via which the processing device presents a graphical user interface comprising options for the user to select to provide the input(s).

However in preferred embodiments the user provides an input by performing a predefined gesture or movement with the user device, and wherein the processing unit is configured to process the measured movements to detect whether the user has performed a predefined gesture or movement with the user device.

In some embodiments, the predefined gesture or movement comprises any of: shaking the user device, turning the user device over, moving the user device in a circle or moving the user device in a figure-of-eight.

Preferably the processing unit is configured such that, when operating in the further mode, the processing unit processes the measured movements obtained during the user-specified time period to identify whether the user has performed one or more movements and/or exercises used to assess fall risk, and in the event that a movement or exercise is identified, the processing unit evaluates how well the user performed said movement or exercise to determine the risk of the user falling.

In some embodiments the processing unit is configured to provide information or feedback to the user based on the determined risk of the user falling.

Preferably the processing unit is configured to continue processing the measured movements to determine if the user has fallen while operating in the further mode.

Preferably the processing unit is configured to switch to operating in the first mode in the event that it is determined that the user has fallen while the processing unit is operating in the further mode.

Preferably the one or more sensors comprise one or more of an accelerometer, air pressure sensor, gyroscope and magnetometer.

In some embodiments the user device further comprises the processing unit. In other embodiments, the processing unit is in a separate unit to the user device.

According to a second aspect of the invention, there is provided a method of operating a fall detection system, the method comprising measuring the movements of a user; operating the system in a first mode in which the measured movements are processed to determine if the user has fallen; and operating the system in a further mode in which the measured movements obtained during a user-specified time period are processed to determine the risk of the user falling.

In preferred embodiments the method comprises the step of detecting a first input from the user specifying the start of the time period during which the user will perform one or more exercises and/or movements used to assess fall risk.

Preferably, on detection of the first input from the user, the method further comprises the step of operating the system in a data collection mode in which measured movements are stored in a memory module for processing when the system is operating in the further mode.

In some embodiments, on detection of the first input from the user specifying the start of the time period, the method comprises the step of starting a timer. In that case, the method further comprises the step of resuming operation of the system in the first mode when the timer reaches a predetermined value.

In alternative embodiments, the method comprises the steps of detecting a second input from the user specifying the end of the time period; and resuming operation of the system in the first mode on detection of the second input.

In some embodiments, the step of operating the system in the further mode is performed following the detection of a third input from the user.

In some embodiments, the method further comprises the step of displaying instructions to the user for one or more exercises and/or movements for the user to perform while the system is operating in the data collection mode.

In some embodiments, the step of displaying comprises adapting the instructions for the one or more exercises and/or movements based on a previously-determined fall risk for the user.

Preferably, the system continues processing the measured movements to determine if the user has fallen while operating in the data collection mode.

Preferably, the method further comprises the step of switching the system to operate in the first mode in the event that it is determined that the user has fallen while the system is operating in the data collection mode.

In some embodiments the method comprises (i) the user pressing a button or key to provide the input(s); or (ii) the user selecting an option on a graphical user interface to provide the input(s).

However in preferred embodiments the method further comprises the steps of the user providing an input by performing a predefined gesture or movement with the, or a part of the, system, and processing the measured movements to detect whether the user has performed a predefined gesture or movement with a user device in the system.

In some embodiments, the predefined gesture or movement comprises any of: shaking the user device, turning the user device over, moving the user device in a circle or moving the user device in a figure-of-eight.

Preferably the step of operating the system in the further mode comprises processing the measured movements obtained during the user-specified time period to identify whether the user has performed one or more movements and/or exercises used to assess fall risk, and in the event that a movement or exercise is identified, evaluating how well the user performed said movement or exercise to determine the risk of the user falling.

In some embodiments the method further comprises providing information or feedback to the user based on the determined risk of the user falling.

Preferably the method further comprises continuing to process the measured movements to determine if the user has fallen while operating in the further mode.

Preferably the method further comprises the step of switching the system to operating in the first mode in the event that it is determined that the user has fallen while the system is operating in the further mode.

According to a third aspect of the invention, there is provided a computer program product having computer-readable code embodied therein, the computer-readable code being configured such that, on execution by a suitable computer or processing unit, the computer or processing unit performs any of the methods described above.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
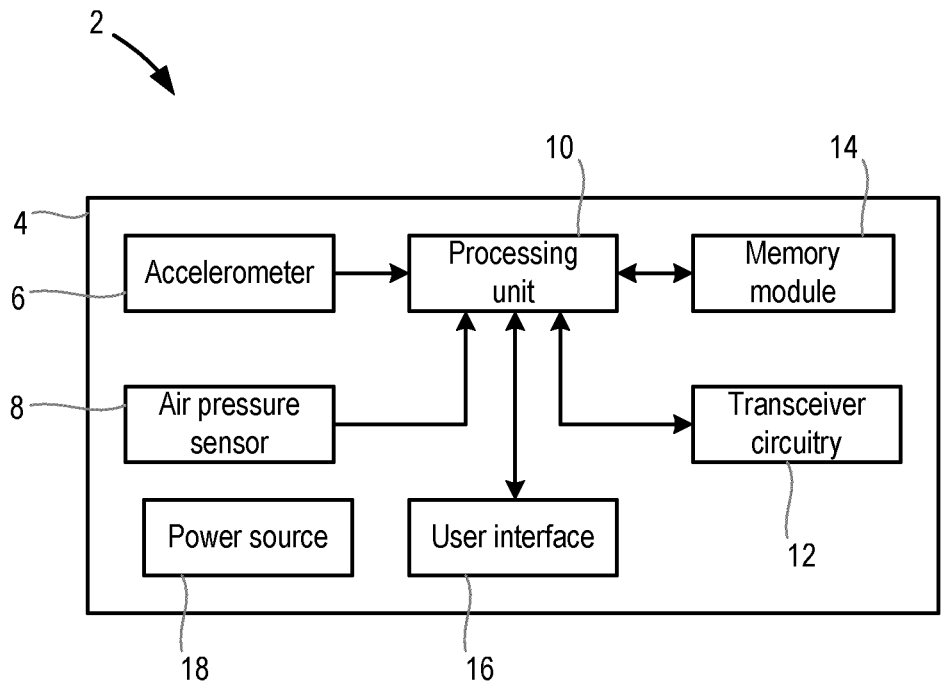
FIG. 1 is a block diagram of a fall detection system according to an embodiment of the invention.

A fall detection system 2 according to an embodiment of the invention is shown in FIG. 1. In this embodiment of the invention, the fall detection system 2 comprises a user device 4 that is designed to be worn or carried by a user.

The user device 4 is preferably in the form of a pendant that is worn on a cord or chain around the user's neck, but it will be appreciated that the user device 4 is not limited to this form factor, and it is possible that the user device 4 could instead be designed to be worn at the user's wrist or waist, on their chest or back, or carried in their pocket.

In this exemplary embodiment, the user device 4 comprises two movement sensors, an accelerometer 6 and an air pressure sensor 8, which are connected to a processing unit 10. The processing unit 10 receives measurements from the movement sensors 6, 8, and processes the measurements to determine if the user of the fall detection system 2 has suffered a fall. The processing unit 10 also controls the operation of the user device 4.

It will be appreciated that the accelerometer 6 measures the accelerations experienced by the user device 4, and the processing unit 10 can analyse the accelerations to identify impacts, determine the speed, change in orientation and/or change in position or height of the user device 4. In certain embodiments, the processing unit 10 can also process the signal from the accelerometer 6 to detect the performance of predetermined gestures (i.e. movements) by the user with the user device 4 (for example shaking the user device 4, moving it in an oscillating motion, a circle, figure of 8, etc.). The signal from the air pressure sensor can be analysed by the processing unit 10 to determine the height and/or change in height of the user device 4.

It will be appreciated that although two movement sensors are shown in this embodiment, fall detection systems according to alternative embodiments may comprise only one movement sensor (for example just the accelerometer 6 with the pressure sensor 8 being omitted). In yet further embodiments, the user device 4 can comprise a gyroscope and/or magnetic field sensor(s) in addition or alternatively to the pressure sensor 8.

The user device 4 also comprises transceiver circuitry 12 that allows the user device 4 to transmit an alarm signal to a remote call centre or the emergency services in the event a fall is detected.

The user device 4 also comprises a memory module 14 that is connected to the processing unit 10 and that can store measurement data from the movement sensors 6, 8, and/or computer readable code for use by the processing unit 10.

It will be appreciated that the memory module 14 may only store the latest measurement data or the measurement data from predefined periods of time (for example indicated by the user as a time period during which they are performing exercises and/or movements as part of a fall risk assessment).

The user device 4 further includes a user interface 16 that provides information to the user and/or allows the user to interact or control the user device 4. The user interface 16 can comprise user input components, such as buttons, keys, switches, trackballs, touch screens or a microphone; and/or user feedback components, such as a speaker, lights, LEDs, a display or a vibration device (for providing tactile feedback to the user). In some embodiments, the user interface 16 comprises at least a dedicated button for the user to press to request help in an emergency (this button is sometimes known as a personal help button).

The user device 4 also comprises a power source 18, such as a battery that provides power to the components of the user device 4.

In alternative embodiments to that shown in FIG. 1, the fall detection system 2 can further comprise a base unit that can be located in the home of the user and that communicates wirelessly with the user device 4. The base unit may also act as a charging station for the user device 4. The base unit may comprise circuitry for enabling communications between the user and a remote call centre (such as the emergency services) via a public switched telephone network and/or a mobile communications network, and/or may provide a connection to the Internet. In some implementations of this system 2, the processing and operations according to the invention can be performed by the processing unit 10 in the user device 4, with the base unit being provided merely to facilitate communications with the remote call centre/emergency services/Internet. In alternative implementations, the user device 4 can communicate the measurements obtained by the movement sensors 6, 8 to the base unit, and a processing unit in the base unit can perform the processing and operations according to the invention using the measurements. This latter embodiment has the advantage that the power consumption of the user device 4 can be substantially reduced.

In yet further embodiments, the user device 4 of the fall detection system 2 can be configured to connect to another electronic device belonging to the user, such as a computer, laptop, tablet or smartphone, to enable the user to control the user device 4 via that electronic device, and/or to enable that electronic device to assist the user in performing the fall risk assessment (for example by displaying information for the user to assist the user in completing the required movements or exercises). In these embodiments, the use of another electronic device to control the user device 4 can replace the need for a user interface 16 to be included in the user device 4 (apart from perhaps a single personal help button). In these embodiments, the other electronic device could also be used to process the movement measurements according to the invention rather than the user device 4 to reduce the power consumption of the user device 4.

In the embodiments where the user device 4 connects to a base unit and/or another electronic device owned by the user, the connection can be made using any known wireless technology, for example Wi-Fi, Bluetooth, Near Field Communication (NFC), etc.

In some embodiments, a remotely-located clinician or other healthcare provider can interact with the user via the user device 4. For example, the clinician or healthcare provider can contact the user via the transceiver circuitry 12 in the user device 4 and advise the user they should perform a fall risk assessment. In this case the clinician or healthcare provider can provide verbal instructions to the user to assist them in completing the required movements and/or exercises.

Figure 2:
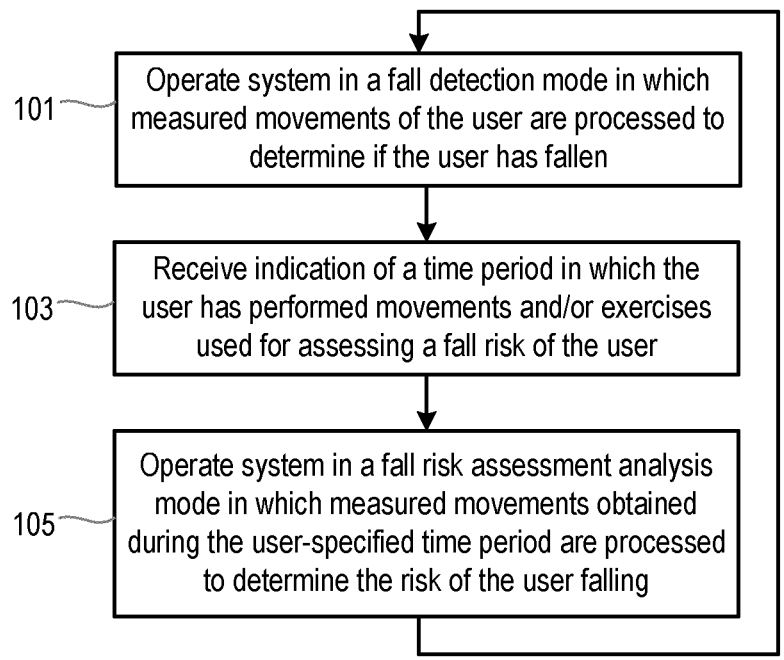
FIG. 2 is a flow chart illustrating a method according to an embodiment of the invention.

FIG. 2 illustrates a method of operating the fall detection system 2 according to the invention. In a first step, step 101, the fall detection system 2 is operated in a fall detection mode in which the measurements of the movements of the user are processed (preferably in real-time or near real-time) to determine if the user has fallen. In this mode, which is also referred to herein as a 'first' or 'normal' mode of operation, the fall detection system 2 operates as a typical fall detector.

In some implementations the processing unit 10 in the user device 4 determines if the user has suffered a fall by extracting values for a feature or various features that are associated with a fall from the movement sensor measurements. For example, the accelerations and air pressure changes experienced by the user device 4 are measured using the accelerometer 6 and air pressure sensor 8, and these measurements are analysed by the processing unit 10 to determine whether the user has suffered a fall.

A fall can be broadly characterised by, for example, a change in attitude of around 0.5 to 1.5 meters (the range may be different depending on the part of the body that the user device 4 is to be worn and the height of the user), culminating in a significant impact, followed by a period in which the user does not move very much. Thus, conventionally, in order to determine if a fall has taken place, the processing unit 10 can process the sensor measurements to extract values for features including one or more of a change in altitude (which can be derived from the measurements from the air pressure sensor 8, but can also or alternatively be derived from the measurements from the accelerometer 6, for example if the air pressure sensor 8 is not present), a maximum activity level (i.e. an impact) around the time that the change in altitude occurs (typically derived from the measurements from the accelerometer 6) and a period in which the user is relatively inactive following the impact (again typically derived from the measurements from the accelerometer 6). It will be appreciated that other features can further improve the detection algorithm. For example, the detection of a change in orientation upon falling can improve the likelihood that the signal is due to a fall.

A fall by the user can be identified where a subset or all of the above features are identified in the measurements. In other words, a fall may be identified where any one or more of the required height change, impact and inactivity period are detected in the measurements.

The analysis performed by the processing unit 10 when operating in the fall detection mode will not be described in further detail herein, but those skilled in the art will be aware of various algorithms and techniques that can be applied to determine whether a user has suffered a fall from accelerometer and/or air pressure sensor measurements.

While the user device 4 is operating in the fall detection mode, the user device 4 may receive an input from the user indicating a time period during which the user is going to or has performed movements and/or exercises for the purposes of estimating their fall risk (step 103).

The input provided by the user is preferably used to indicate when the time period is to start. In some embodiments, a further input by the user can be understood by the processing unit 10 as indicating the end of the time period. Alternatively, the time period can have a predetermined length measured by a timer, in which case the user may only be required to provide an input indicating the start of the time period. The use of the timer ensures that the user device 4 is not storing data for an unnecessarily long time period.

During the time period, and more specifically when the movements of the user are being measured during the time period, the fall detection system 2 is referred to herein as operating in a fall risk assessment data collection mode or the 'second' mode. This is the mode the device 4 operates in following receipt of the input from the user indicating that they will perform certain movements and/or exercises for the purposes of assessing fall risk. In this mode, the user device 4 stores the measurements obtained by the movement sensors 6, 8 in the memory module 14 for subsequent analysis to determine the fall risk.

In some embodiments, the user interface 16 in the user device 4 can present information to the user to assist them in performing the fall risk assessment when the fall risk assessment data collection mode is entered. In particular, the user interface 16 can present information indicating the specific movement(s) and/or exercise(s) that the user should perform, and/or provide instructions to the user on how to perform the movement or exercise.

While the user device 4 is operating in the data collection mode and storing the movement measurement data collected during the user-specified time period, the user device 4 is preferably still processing the measurements of the movement of the user in real-time or near real-time in order to determine if the user has fallen (the same as if the user device 4 was operating in the fall detection mode). If the fall detection system 2 detects a fall while in the data collection mode, an alarm is triggered in the normal way (i.e. as if the system 2 was operating in the fall detection mode). In other, less-preferred embodiments, the user device 4 may not process the measurements of the user to determine if the user has fallen while operating in the fall risk assessment data collection mode.

The user input providing the indication of the time period may be provided to the user device 4 by, for example, the user pressing a button or key on the user device 4, performing a predetermined gesture with the user device 4, selecting an option within a graphical user interface, or providing the indication via a further electronic device, such as a computer, laptop, tablet or smartphone.

Although it was noted above that the input provided by the user preferably indicates when the time period is to start, in another alternative, the user may be able to provide an input at the end of a time period during which they have performed the movements and/or exercises. In this alternative, it is necessary for the user device 4 to temporarily store movement measurement data in the memory module 14 for at least the duration of the predetermined time period so that the measurements are available if an input is subsequently received from the user.

After the end of the time period has passed (and more specifically after movements of the user have been measured for the time period), the system 2 returns to operating in the fall detection mode.

Subsequently, the system 2 is operated in a fall risk assessment data analysis mode (also referred to as the 'third' or 'further' mode) in which the movements measured during the user-specified time period are processed to determine or estimate the fall risk for the user (step 105).

In some embodiments the system 2 can automatically switch to operating in the data analysis mode after the movement measurements for the predetermined time period have been collected (in which case the fall risk assessment data collection mode and fall risk assessment data analysis mode can be considered as a single mode of operation). In other embodiments, the system 2 can be switched into operating in the data analysis mode on receipt of an input from the user. In yet further embodiments, the system 2 can be automatically or manually switched to operating in the data analysis mode after movement measurements have been collected for a plurality of separate time periods.

In the embodiments in which the user switches the system 2 into the fall risk assessment data analysis mode, the input from the user can be provided in a similar way to that used to indicate the time period during which the user performed the movements and/or exercises. That is, the input could comprise, for example, the user pressing a (or another) button or key on the user device 4, performing the or another predetermined gesture with the user device 4, selecting an option within a graphical user interface, or providing the indication via an input on a further electronic device, such as a computer, laptop, tablet or smartphone.

As with the fall risk assessment data collection mode, while the system 2 is operating in the fall risk assessment data analysis mode the system 2 may continue to measure the movements of the user and process the measurements in real-time or near real-time in order to detect if the user falls. If the fall detection system 2 detects a fall while in the data collection mode, an alarm is triggered in the normal way (i.e. as if the system 2 was operating in the fall detection mode).

In the fall risk assessment data analysis mode, the movement measurements collected since the last time the system 2 was operated in the data analysis mode (which may relate to one user-specified time period or multiple user-specified time periods) are processed by the processing unit 10 to identify certain movement(s) and/or exercise(s) that the user should perform to assess their fall risk. For any movement(s) and/or exercise(s) identified in the measurements, the processing unit 10 assesses the user's performance of the identified movement(s) and/or exercise(s).

There are a number of different movement(s) and/or exercise(s) that the user could perform as part of a fall risk assessment. Each movement or exercise can test the user's walking ability, their balance, strength or reaction time, or any combination of these. Examples of suitable movement(s) and/or exercise(s) include the user standing still in various ways (e.g. feet together, near tandem, tandem, one leg, etc.), walking, a sit-to-stand transfer (i.e. standing up from a sitting position), a timed-up-and-go test (i.e. timing how long it takes the user to stand up, walk a certain distance and then return to a sitting position on the chair), and a reaction test involving timing how long it takes the user to react to a visual and/or audible stimulus from the user device 4, picking up an object from a low level (e.g. the floor), or turning around some predetermined angle (e.g. 360 degrees). As indicated below, each of these movements or exercises can be performed by the user with different levels of difficulty to provide a better indication of the fall risk of the user. These movements and exercises are also typically included as part of a fall prevention exercise program to help the user reduce their risk of falling over time.

The use of these movement(s) and/or exercise(s) in assessing fall risk are known in the art, as are techniques for identifying them in measurements of the movement of a user and for analysing how well the user has performed them, so detailed techniques for processing the movement measurements are not provided herein.

Figure 3:
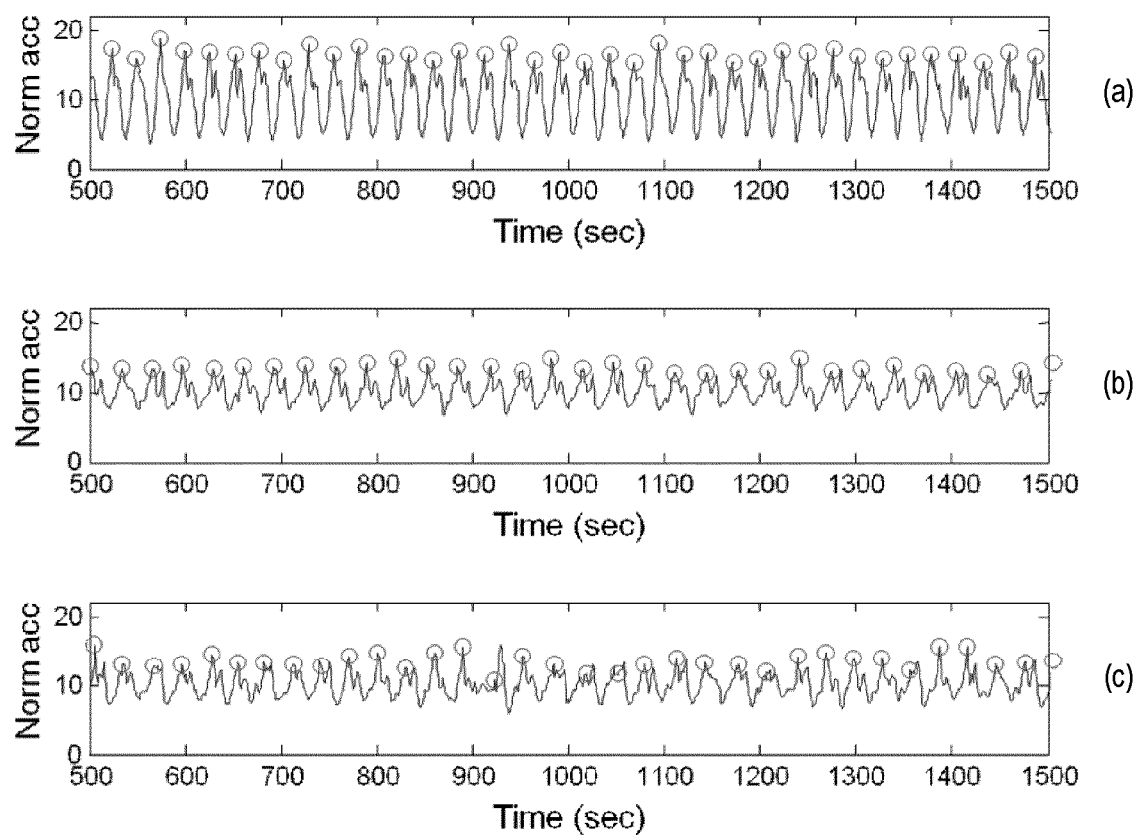
FIG. 3 is a set of graphs indicating movement measurements obtained when a user performs three variants of a walking test.

FIG. 3 shows the movement measurements obtained for a user that performed three variants of a walking exercise. Each graph in FIG. 3 plots the norm of the three-dimensional acceleration measurements against time, and the circles shown on various peaks are heel-strikes by the user (i.e. the acceleration caused by the heel of the user striking the ground as they walk) that are identified by the processing unit 10. FIG. 3(a) shows the norm of the acceleration measured when the user was walking normally (for the user), FIG. 3(b) shows the norm of the acceleration measured when the user was requested to walk slower than normal, and FIG. 3(c) shows the norm of the acceleration measured when the user was requested to walk slower and to walk less 'regularly' (e.g. to vary the pace and stride length as they walked). The forced slower pace of walking produced a more irregular acceleration pattern (as shown in FIG. 3(b)) than the normal walking shown in FIG. 3(a), with an even more pronounced irregular acceleration pattern being shown in FIG. 3(c) when the user walked slowly with an irregular pace/stride length. Users at different levels of fall risk are likely to show a similar deterioration in the steadiness of their walking in the acceleration measurements as they perform the walking tests and users at a higher risk of falling are expected to show more unsteady walking patterns in each test compared to users at a lower risk of falling. Thus, in practice, by analysing how the user performed each walking exercise (either by analysing each exercise in isolation or with reference to a 'model' user or to the other walking exercises by the user), the fall risk of the user can be estimated. In particular, a generally slower walking speed and/or more unstable/less regular walking pattern indicate a higher risk of falling.

Figure 4:
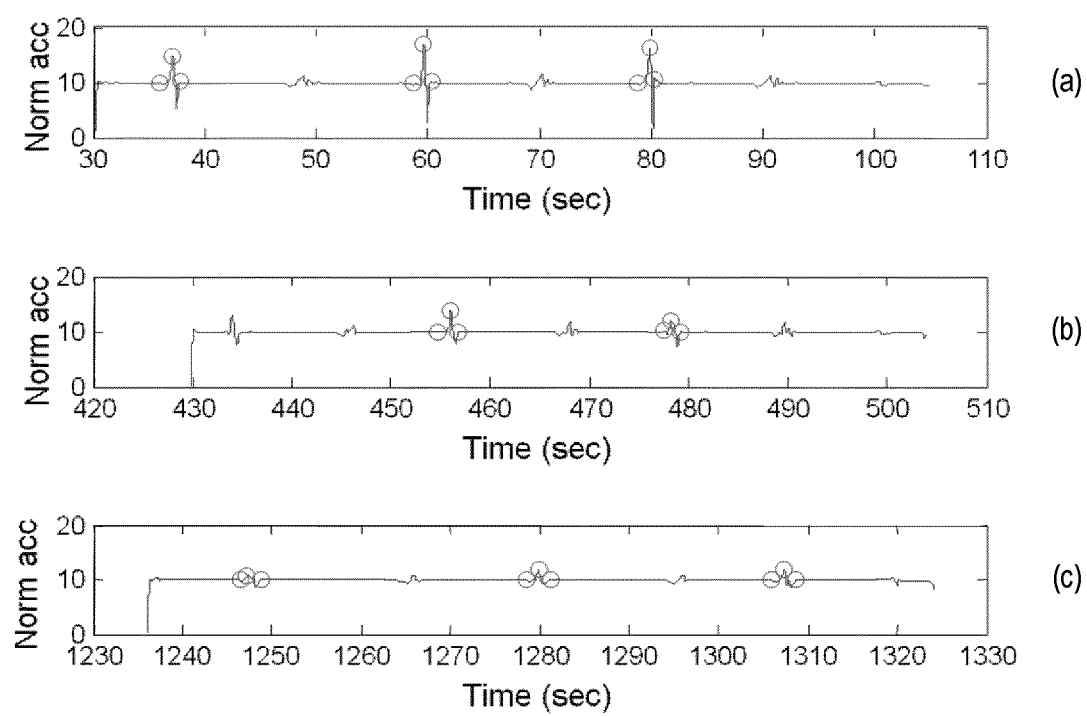
FIG. 4 is a set of graphs indicating movement measurements obtained when a user performs three variants of a sit-to-stand transfer test.

FIG. 4 shows the movement measurements obtained for a user that performed three variants of a sit-to-stand (STS) transfer exercise. Each graph in FIG. 4 plots the norm of the three-dimensional acceleration measurements against time, and the circles shown on various parts of the signal are movements associated with a STS transfer that are identified by the processing unit 10. FIG. 4(a) shows the norm of the acceleration measured when the user stood up from a chair normally (for the user), FIG. 4(b) shows the norm of the acceleration measured when the user was requested to stand up slower than normal, and FIG. 4(c) shows the norm of the acceleration measured when the user was requested to stand up from a chair even more slowly. Users at a higher risk of falling are expected to show a lower total power output in each test compared to users at a lower risk of falling. By analysing how the user performed each STS transfer exercise (either by analysing each exercise in isolation or by reference to a model user or the other exercises), for example including estimating the power used by the user in performing the exercise, the fall risk of the user can be estimated. In particular, a generally longer duration to stand up, and/or the exertion of less power by the user in standing up indicates a higher risk of falling.

Figure 5:
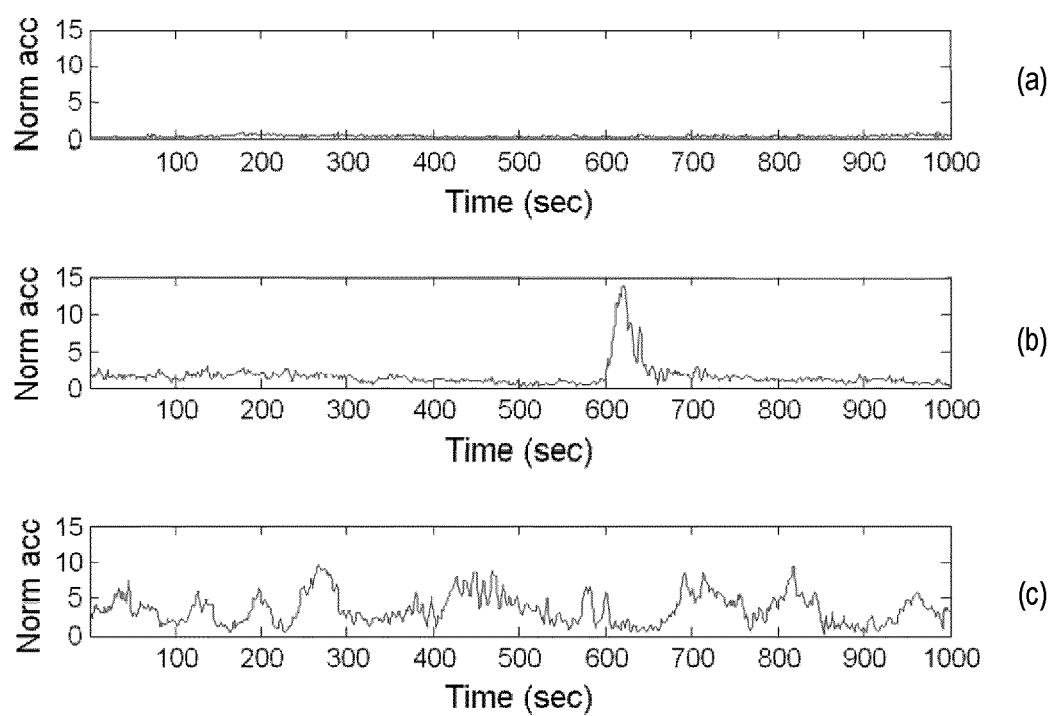
FIG. 5 is a set of graphs indicating movement measurements obtained when a user performs three variants of a standing test.

FIG. 5 shows the movement measurements obtained for a user that performed three variants of a standing exercise. Each graph in FIG. 5 plots the norm of the three-dimensional acceleration measurements against time. FIG. 5(a) shows the norm of the acceleration measured when the user was standing still (although alternatively the graph can show the measured acceleration after low-pass filtering, with the low-pass components optionally normalised), FIG. 5(b) shows the norm of the acceleration measured when the user was standing on one leg, and FIG. 5(c) shows the norm of the acceleration measured when the user was standing on one leg with their eyes closed. Standing on one leg produced a more irregular acceleration pattern (as shown in FIG. 5(b)) than the normal standing shown in FIG. 5(a), representing the fact that the user was having to keep adjusting their body posture to keep their balance, with an even more irregular acceleration pattern being shown in FIG. 5(c) when the user stood on one leg with their eyes closed. Users at different levels of fall risk are likely to show a similar deterioration in their ability to remain balanced and steady as they perform the different standing tests and users at a higher risk of falling are expected to show more unsteady patterns in each test compared to users at a lower risk of falling. Thus, in practice, by analysing how the user performed each standing exercise (either by analysing each exercise in isolation or by reference to a model user or the other exercises), the fall risk of the user can be estimated. In particular, a generally higher amount of sway by the user when performing the test (as indicated by non-zero acceleration) indicates a higher risk of falling.

Once a fall risk has been calculated for the user, either from one type of movement or exercise performed by the user, or from multiple types of movement or exercise, the fall detection system 2 can provide information or feedback to the user or to a remotely-located clinician based on the calculated fall risk. This information or feedback can be provided to the user via the user interface 16 of the user device 4, or via other means, such as a base unit or associated electronic device (if present in the system 2).

The information may comprise, for example, an indication of the fall risk (e.g. high, medium, low), how the user compares to previous iterations of the movement or exercise by the user (e.g. improved, same/similar, worsened), how the performance of the user compares to a target performance (for example specified in a fall prevention exercise program).

After calculating the fall risk for the user, the user device 4 returns to operating in the normal fall detection mode until the next input is received from the user indicating that they are going to perform the movements or exercises for fall risk assessment.

As noted above, the user provides an input indicating when they are going to (or have) perform movements and/or exercises in order to assess their fall risk to the user device 4 so that the user device 4 can enter the fall risk assessment data collection mode. In some embodiments the user also provides an input to the user device 4 to control the device 4 to enter the analysis mode and to calculate the fall risk from the collected data.

This/these input(s) can be provided by the user pressing a button or key on the user device 4, or by pressing a button or key on the base unit or other electronic device (if they form part of the system 2). However, in embodiments where the user device 4 comprises a single button for allowing the user to summon help in an emergency, providing this button with dual functions (i.e. summoning help and indicating the start of a fall risk assessment) may be confusing to the user.

Thus, in preferred embodiments the user provides the input to the user device 4 by performing a predetermined gesture with the user device 4. For example, the user input can comprise shaking the user device 4, moving it in a circle or figure-of-8, turning the device 4 over or performing any other simple predefined motion. The gesture can be detected in the measurements from the accelerometer 6 by the processing unit 10. Where the user is to provide a further input to the user device 4 (for example to indicate the end of the fall risk assessment data collection mode and/or to initiate the fall risk assessment data analysis mode), the gesture used to provide this indication may be the same as that used to initiate the fall risk assessment data collection mode, or it may be a different gesture.

In embodiments where the user device 4 (or optionally a base unit or another electronic device if they are part of the system) provides instructions to the user to assist them in performing the movements or exercises required for the fall risk assessment, it is possible for the movements or exercises to be adapted based on the previous performance of those tests by the user. In particular, if a user previously performed an exercise well (i.e. the test results indicated a low fall risk), then the instructions/exercise can be adapted so that the user performs a more difficult version of the exercise next time. Likewise, if the user previously performed an exercise poorly (i.e. the test results indicated a high fall risk), then the instructions/exercise can be adapted so that the user performs an easier version of the exercise next time. For example, in the case of a standing test, increasing the difficulty can mean instructing the user to stand with their feet closer together than in the previous test or with one foot in front of the other.

Figure 6:
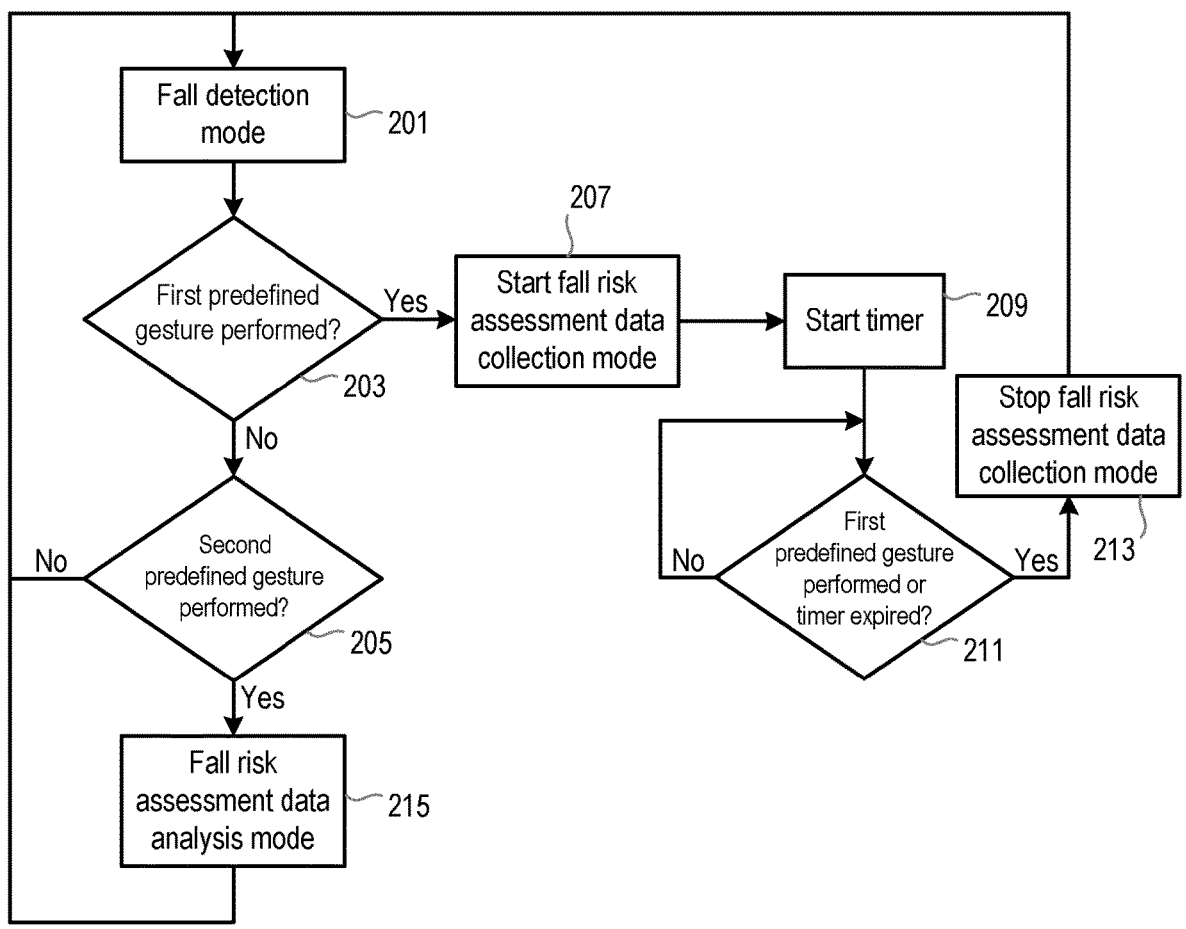
FIG. 6 is a flow chart illustrating the operation of the system according to an exemplary embodiment of the invention.

A flow chart illustrating the operation of the user device 4 according to an embodiment of the invention is shown in FIG. 6. In this embodiment, a user input in the form of a first predefined gesture is used to indicate the start and end of the fall risk assessment data collection mode and a user input in the form of a second predefined gesture is used to initiate the fall risk assessment data analysis mode. Also in this embodiment, the processing unit 10 is continuously analysing the measurements from the movement sensors to determine if the user has fallen. If a fall is detected (or a personal help button pressed), an alarm is triggered and the user device 4 requests help for the user from a call centre or from the emergency services. If a fall is detected (or the personal help button pressed) at any point during the fall risk assessment data collection or data analysis modes, the data collection or data analysis mode is interrupted and the processing unit 10 again triggers the alarm and requests help for the user.

In the first step, step 201, the user device 4 is operating in the normal mode of operation, i.e. it is measuring the movements of the user and is analysing those measurements to determine if the user has fallen.

While analysing the measurements of the movements, the processing unit 10 is also analysing the measurements to detect whether the user has performed a first predefined gesture required to initiate the fall risk assessment data collection mode (step 203) or a second predefined gesture required to initiate the fall risk assessment data analysis mode (step 205).

If the user does perform the first predefined gesture (and it is detected by the processing unit 10), then the processing unit 10 enters or starts the data collection mode (step 207). During this mode the user can be presented with instructions to assist them in performing the required movements or exercises and the measurements of the movements of the user are stored for subsequent analysis. On entering the data collection mode, a timer is started (step 209). The timer may, for example, have a value of 2 minutes.

Assuming that no fall is detected and the personal help button is not pressed while the device 4 is in the data collection mode, it is determined whether the first predefined gesture has been performed by the user again to signify the end of the specified movement or exercises or whether the predetermined timer (e.g. 2 minutes) has expired (step 211). If neither have occurred yet, the data collection mode continues and the process loops back to step 211 until one of these events occurs. If the first predefined gesture is detected or the timer expires, the data collection mode is stopped (step 213) and the device 4 returns to the fall detection mode (step 201).

If at step 203 the first predefined gesture has not been performed, or following a return to the fall detection mode (step 201) a further occurrence of the first predefined gesture has not occurred, then the processing unit assesses whether the second predefined gesture has been performed (step 205). If not, the device 4 remains in the fall detection mode (step 201).

If the user does perform the second predefined gesture, the device 4 switches into the fall risk assessment data analysis mode in which the measurements collected during the previous data collection modes is analysed to determine the fall risk for the user (step 215). On completion of the data analysis, the device 4 returns to operating in the fall detection mode (step 201).

Figure 7:
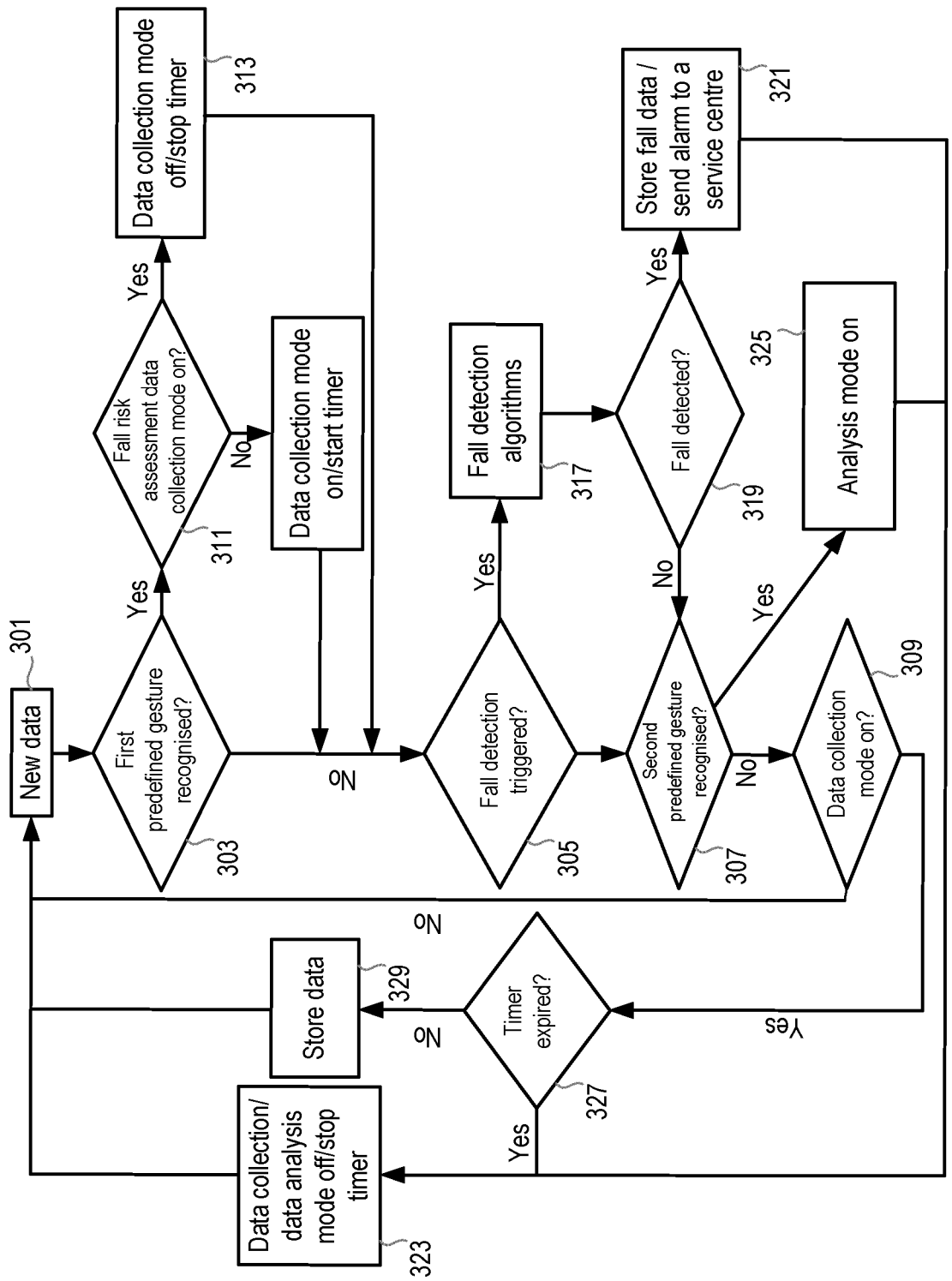
FIG. 7 is a flow chart illustrating the operation of the system according to another exemplary embodiment of the invention.

A more detailed method of operating a user device 4 according to an embodiment of the invention is shown in FIG. 7. In this embodiment, the fall detection mode comprises two levels of processing. In a first, low power stage, the processing unit 10 analyses the measured accelerations for a single easily-detected characteristic of a fall, such as an impact (e.g. an acceleration greater than a threshold value). This low-power processing can be performed for each new block of measurement data. If at any time the characteristic is detected, the processing unit 10 activates the full fall detection processing and the measurements are processed to detect whether other characteristics of a fall are present, such as a free-fall, height change, change in orientation, etc.

In FIG. 7, for each block of new measurement data (301) the processing unit 10 checks if a first predefined gesture is recognized (e.g. turning the device 4 to start or stop the data collection mode) (303). If the first predefined gesture is not recognized, the processing unit 10 checks if the fall detection algorithm should be triggered (305). If not, the processing unit 10 checks whether the second predefined gesture is recognized (e.g. shaking the device to start the analysis mode) (307). If not, the processing unit 10 checks if the device 4 is already in the fall risk assessment data collection mode (309). If not, the user device 4 continues operating in the fall detection mode (and in particular using the low-power processing of the measurement data), meaning that no data is stored in the user device 4, no timers are running, and the full fall detection algorithm is not running and no stored data is being analysed to determine fall risk. It will be appreciated that the checks in 303 (for the first predefined gesture being performed), 305 (for the fall detection being triggered) and 307 (for the second predefined gesture being performed) can be performed in a different order to that shown in FIG. 7. It will also be appreciated that the checks can be performed at the same time rather than in series.

If at 303 the first predefined gesture is recognized, the user device 4 checks whether the device 4 is already operating in the fall risk assessment data collection mode (311). If so, the data collection mode is stopped and the timer deactivated (313). If not, the data collection mode is started and the timer started (315). During the data collection mode data is stored and the timer is running.

If at 305 it is determined that the full fall detection algorithm is required then the processing unit 10 processes the measurements to determine if the user has fallen (317 and 319). If a fall is detected, the measurement data relating to the fall can be stored for later analysis, an alarm can be triggered and help requested from a call centre or emergency service (321). Then in 323 the data collection mode (or data analysis mode if active) is stopped and any timer stopped. The device 4 is then operating in the normal fall detection mode when new data is received (301).

If no fall is detected at 319 or the full fall detection processing is not triggered at 305, then the processing unit 10 checks for the second predefined gesture (307). If the second predefined gesture is recognized in the measurement data, then the user device 4 operates in the data analysis mode (325) in which all data stored during the or any data collection mode since the last time the data analysis mode was performed is processed to determine the fall risk. If the data analysis mode is activated in 325, the data collection mode (if still active) is switched off and any running timer stopped (323).

If the second predefined gesture is not recognised at 307, but at 309 the data collection mode is determined to be active, then it is checked at 327 whether the timer has expired (i.e. it is checked whether the time elapsed since the start of the data collection has reached a threshold value). If the timer has expired, then the data collection mode is deactivated (323). If the timer has not yet expired, then the block of data received at 301 is stored (329).

The process then repeats for the next block of measurement data (301). The next block of measurement data may be contiguous with the previous block of measurement data (i.e. with no gaps between the blocks of data), non-contiguous with the previous block of measurement data or overlapping with the previous block of measurement data (e.g. the oldest sample or set of samples in the previous block of data can be discarded and a new sample or set of samples added to the remaining samples to form the next block of measurement data). Non-contiguous blocks of measurement data may be used where, for example, little or no movement is detected in the previous block of measurement data (e.g. because the user is lying or sitting down), which reduces the power consumption of the user device 4.

Although not shown in FIG. 7, if at any point a personal help button on the user device 4 is pressed by the user, the process moves straight to 321 and an alarm is triggered and help requested for the user by the user device 4.

There is therefore provided a system and method that enables a user to quickly and easily obtain an estimate of their fall risk in a home or other non-clinical environment using a generally unobtrusive user worn or carried device.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not execute other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection system designed to be worn or carried by a user, comprising:
   a user device comprising one or more sensors configured to measure movements of the user;
   a memory device; and
   a processing unit configured to:
      operate in a first mode in which the processing unit processes the measured movements to determine if the user has fallen;
      detect a first input from the user specifying a start of a user-specified time period, wherein the user-specified time period has a predetermined length during which the user will perform one or more specified exercises and/or movements used to assess fall risk;
      operate in a data collection mode in which the processing unit stores a sub-set of the measured movements, which includes only the measured movements obtained during the user-specified time period having the predetermined length, in the memory device;
      detect a subsequent input from the user specifying a subsequent start of a subsequent user-specified time period, wherein the subsequent user-specified time period has a subsequent predetermined length during which the user will perform the one or more specified exercises and/or movements used to assess the fall risk;
      operate in the data collection mode in which the processing unit stores a subsequent sub-set of the measured movements, which includes only the measured movements obtained during the subsequent user-specified time period having the subsequent predetermined length, in the memory device;
      detect a second different input from the user after lapse of the user-specified time period; and
      operate in a data analysis mode in which the processing unit processes the sub-set of the measured movements stored in the memory device and the subsequent sub-set of the measured movements stored in the memory device to determine a risk of the user falling.

2. The fall detection system as claimed in claim 1, the processing unit is configured to concurrently operate in the first mode and in the data collection mode.

3. The fall detection system as claimed in claim 1, wherein on detection of the first input from the user specifying the start of the time period, the processing unit is further configured to start a timer.

4. The fall detection system as claimed in claim 3, wherein the processing unit is configured to resume operating in the first mode when the timer reaches a predetermined value.

5. The fall detection system as claimed in claim 1, the system further comprising a display that is controlled by the processing unit, the processing unit being configured to provide instructions to the user via the display for one or more exercises and/or movements for the user to perform while the processing unit is operating in the data collection mode.

6. The fall detection system as claimed in claim 5, wherein the processing unit is configured to adapt the instructions for the one or more exercises and/or movements based on a previously-determined fall risk for the user.

7. The fall detection system as claimed in claim 1, wherein the processing unit is configured to continue processing the measured movements to determine if the user has fallen while operating in the data collection mode.

8. The fall detection system as claimed in claim 1, wherein the user provides an input by performing a predefined gesture or movement with the user device, and wherein the processing unit is configured to process the measured movements to detect whether the user has performed a predefined gesture or movement with the user device.

9. The fall detection system as claimed in claim 8, wherein the predefined gesture or movement comprises one of: shaking the user device, turning the user device over, moving the user device in a circle or moving the user device in a figure-of-eight.

10. The fall detection system as claimed in claim 1, wherein the processing unit is configured such that, when operating in the analysis mode, the processing unit processes the measured movements obtained during the user-specified time period to identify whether the user has performed one or more movements and/or exercises used to assess fall risk, and in the event that a movement or exercise is identified, the processing unit evaluates how well the user performed said movement or exercise to determine the risk of the user falling.

11. The fall detection system as claimed in claim 1, wherein the processing unit is configured to continue processing the measured movements to determine if the user has fallen while operating in the data analysis mode.

12. The fall detection system as claimed in claim 1, further comprising:
a user interface, wherein the processing unit is further configured to provide an indication of a level of the determined fall risk with the user interface.

13. The fall detection system as claimed in claim 1, wherein the one or more sensors are from a group consisting of an accelerometer, a pressure sensor, a gyroscope, and a magnetic field sensor.

14. The fall detection system as claimed in claim 1, wherein the user device is from a group consisting of a pendant, a wrist band, and chest band.

15. A method of operating a fall detection system designed to be worn by a user, the method comprising:
measuring, with one or more sensors of a user device, movements of the user;
operating, with a processing unit of the user device, the system in a first mode in which the measured movements are processed to determine if the user has fallen;
detecting, with the processing unit of the user device, a first input from the user specifying a start of a user-specified time period, wherein the user-specified time period has a predetermined length during which the user will perform one or more specified exercises and/or movements used to assess fall risk;
operating, with the processing unit of the user device, the system in a data collection mode in which the processing unit stores a sub-set of the measured movements, which includes only the measured movements obtained during the user-specified time period having the predetermined length, in a memory;
detecting, with the processing unit of the user device, a subsequent input from the user specifying a subsequent start of a subsequent user-specified time period, wherein the user-specified time period has a subsequent predetermined length during which the user will perform the one or more specified exercises and/or movements used to assess the fall risk; and
operating, with the processing unit of the user device, in the data collection mode in which the processing unit stores a subsequent sub-set of the measured movements, which includes only the measured movements obtained during the subsequent user-specified time period having the subsequent predetermined length, in the memory;
detecting, with the processing unit of the user device, a second different input from the user after lapse of the user-specified time period; and
operating, with the processing unit of the user device, the system in a data analysis mode in which the processing unit processes the stored sub-set of the measured and the stored subsequent sub-set of the measured movements to determine a risk of the user falling.

16. The method as claimed in claim 15, wherein the user performs a gesture to input the start of the time period.

* * * * *